US00PP22304P2

(12) United States Plant Patent
Horvath et al.

(10) Patent No.: US PP22,304 P2
(45) Date of Patent: Dec. 6, 2011

(54) ***POLYGONATUM* PLANT NAMED 'PRINCE CHARMING'**

(50) Latin Name: *Polygonatum biflorum×Polygonatum humile*
Varietal Denomination: Prince Charming

(76) Inventors: Brent A. Horvath, Fontana, WI (US); Therese LaLonde Horvath, Fontana, WI (US)

( * ) Notice: Subject to any disclaimer, the term of this patent is extended or adjusted under 35 U.S.C. 154(b) by 0 days.

(21) Appl. No.: 12/807,525

(22) Filed: Sep. 8, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — Penny J. Aguirre

(57) ABSTRACT

A new cultivar of *Polygonatum* named 'Prince Charming' characterized by its height of about 30 cm (12 inches), its heavy and early blooming habit, its ability to bloom as a young plant, and its pronounced ridge (ligule) at the point of stem attachment on the lower leaf surface

2 Drawing Sheets

Genus and species: *Polygonatum biflorum×Polygonatum humile.*

Cultivar: 'Prince Charming'.

BACKGROUND OF THE INVENTION

The present invention relates to a new and distinct cultivar of *Polygonatum biflorum×Polygonatum humile* and will be referred to hereafter by its cultivar name, 'Prince Charming'. 'Prince Charming' represents a new herbaceous perennial grown for use as a landscape plant.

'Prince Charming' arose as a selection from seed sown from open pollination of an unnamed plant of *Polygonatum biflorum* in a field plot of *Polygonatum* in Hebron, Ill. The exact parentage of 'Prince Charming' is unknown, however it is believed to be a hybrid between *Polygonatum biflorum* and *Polygonatum humile* based on its characteristics and the presence of *Polygonatum humile* in the growing area. The Inventor selected 'Prince Charming' as a single unique plant in 2003.

Asexual reproduction of the new cultivar was first accomplished by division in Hebron, Ill. in 2004 by the Inventor. Asexual reproduction by division and in vitro propagation has determined that characteristics of this cultivar are stable and are reproduced true to type in successive generations.

SUMMARY OF THE INVENTION

The following traits have been repeatedly observed and represent the characteristics of the new cultivar. These attributes in combination distinguish 'Prince Charming' as unique from all other selections and forms of *Polygonatum* known to the Inventor.

1. 'Prince Charming' attains a height of about 30 cm (12 inches), intermediate in height between the parent species.
2. 'Prince Charming' blooms early in the season, commencing in May in Illinois.
3. 'Prince Charming' blooms reliably as a young plant.
4. 'Prince Charming' exhibits a pronounced ridge (ligule) at the point of stem attachment on the lower leaf surface.

'Prince Charming' can be most closely compared to the parent plants. 'Prince Charming' differs from the female parent, an unnamed plant of *Polygonatum biflorum,* in being shorter in height (*Polygonatum biflorum* is typically 2 to 4 feet in height), in having smaller foliage, in blooming earlier in the season (May versus June) with more blooms, in having shorter stem internodes, and in exhibiting a pronounced ligule at leaf attachment. 'Prince Charming' differs from the probable male parent, an unnamed plant of *Polygonatum humile,* in being taller in height, and in having leaves that are lighter in color, more round in shape, and larger in size. 'Prince Charming' can be compared to *Polygonatum* cultivars 'Angel Wing' (U.S. Plant Pat. No. 21,543), 'Double Stuff' (U.S. Plant Pat. No. 19,624), and 'Kelli's Gold' (U.S. Plant Pat. No. 15302). 'Angel Wing' differs from 'Prince Charming' in having variegated foliage. 'Double Stuff' differs from 'Prince Charming' in having variegated foliage and red stems. 'Kekli's Gold' differs from 'Prince Charming' in having golden colored foliage.

BRIEF DESCRIPTION OF THE DRAWING

The accompanying colored photographs illustrate the overall appearance and distinct characteristics of the new *Polygonatum,* 'Prince Charming', as grown outdoors in a garden in Hebron, Ill. The plant is approximately three years in age from a single division.

BOTANICAL DESCRIPTION OF THE PLANT

Figure 1:
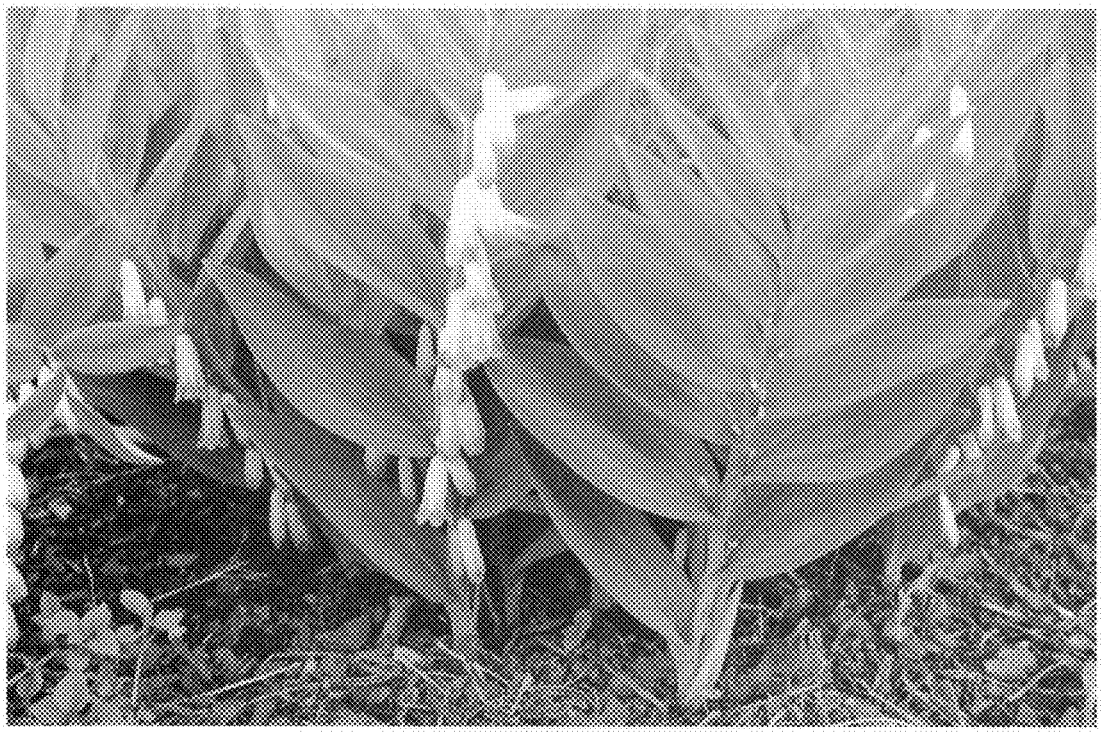
FIG. 1 provides a view of 'Prince Charming' in bloom.
Figure 2:
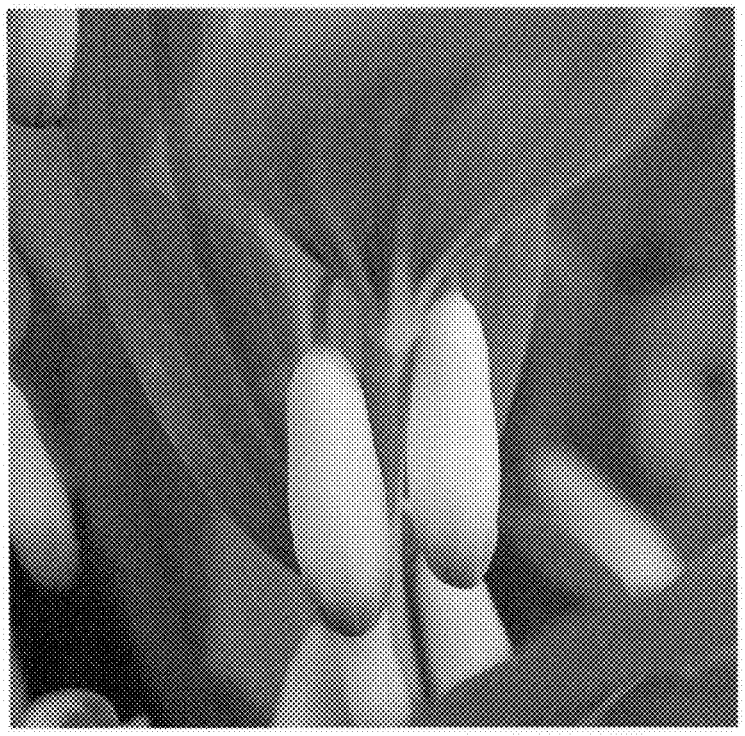
FIG. 2 provides a close-up view of the flowers of 'Prince Charming'.
Figure 3:
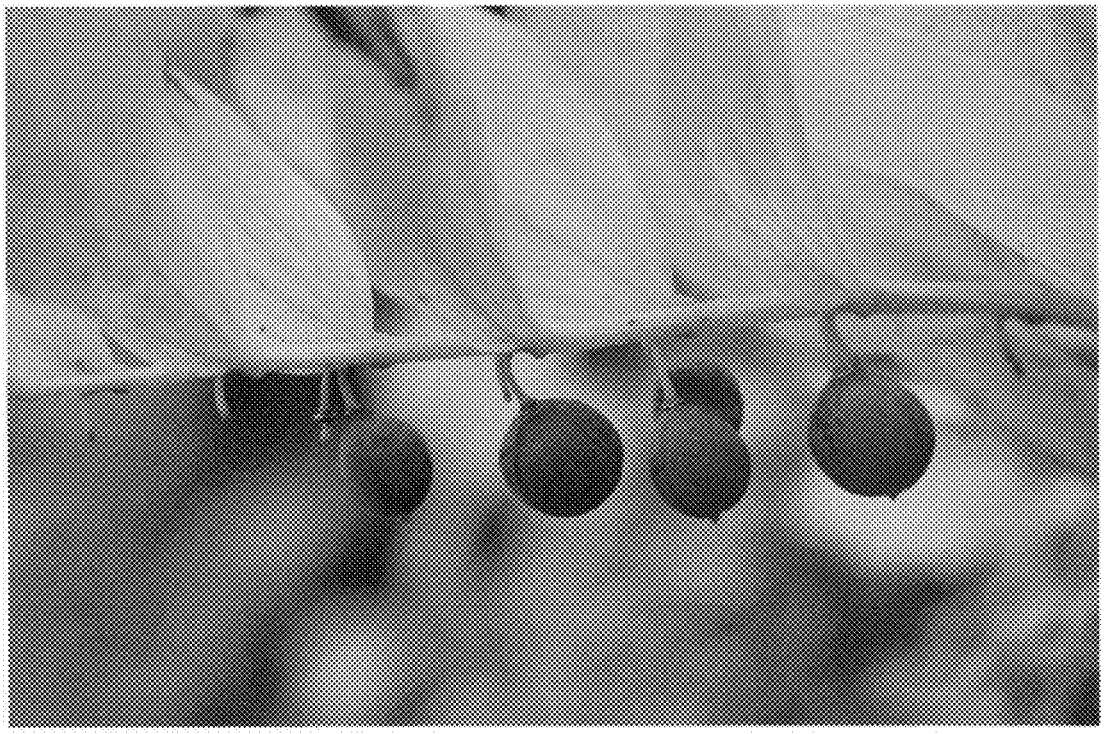
FIG. 3 provides a close-up view of the fruit (berries) of 'Prince Charming'. The colors in the photographs are as close as possible with the digital photography and printing techniques utilized and the color codes in the detailed botanical description more accurately describe the new *Polygonatum.*

The following is a detailed description of three year-old plants of 'Prince Charming' as grown outdoors in Hebron, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—About 3 weeks in late spring.

*Plant habit.*—Herbaceous, rhizomatous, clump-forming perennial, primarily upright with flowers secund.

*Height and spread.*—About 30 cm in height and width.

*Hardiness.*—At least to U.S.D.A. Zone 4.

*Diseases and pests.*—No susceptibility to diseases or pests has been observed, plants of the genus *Polygonatum* typically do not have disease and pest problems.

*Root description.*—Fleshy roots arising from knotty rhizomes; an average of 2.5 cm in length and 1 cm in diameter, dull and knobby surface texture, 161B in color.

Growth and propagation:

*Propagation.*—Rhizome division and tissue culture.

*Growth rate.*—Vigorous.

Stem description:

*Shape.*—Round to slightly winged and ridged, solid.

*Stem color.*—138C.

*Stem size.*—Approximately 5 mm in diameter, up to about 30 cm in length.

*Stem surface.*—Glabrous and glaucous.

*Branching.*—Caulescent, un-branched stems emerge from rhizome.

*Internode length.*—1 to 4 cm.

Foliage description:

*Leaf shape.*—Broadly elliptic.

*Leaf division.*—Simple.

*Leaf base.*—Leaf blade cuneate and base sheathed to stem.

*Leaf apex.*—Acuminate.

*Leaf venation.*—Parallel, slightly recessed on upper surface, prominently ridged on lower surface, 138B to 138C in color on upper and lower surface.

*Leaf margins.*—Entire.

*Leaf attachment.*—Sessile and sheathed.

*Leaf arrangement.*—Alternate.

*Leaf surface.*—Glabrous, slightly glaucous.

*Leaf color.*—Immature and mature upper surface; 138A, immature and mature lower surface; 138B, fall foliage; 20B to 11C.

*Leaf size.*—4.5 to 7.5 cm in length, 1.5 to 2.5 cm in width.

*Leaf quantity.*—An average of 14 per stem.

Flower description:

*Inflorescence type.*—Pendent, cymose clusters of tubular flowers.

*Lastingness of inflorescence.*—Determinate, blooms last approximately 2 weeks.

*Inflorescence size.*—About 2.5 cm in depth and 1.5 cm in width.

*Flower fragrance.*—Slightly sweet scented.

*Flower type.*—Tubular, comprised of 6 fused tepals with distal 6 mm portion un-fused to create an aperture of about 6 mm when fully open.

*Flower aspect.*—Downward on pendant peduncles.

*Flower size.*—About 2.3 cm in depth and 7 mm in width.

*Flower number.*—1 to 3 per internode, up to about 19 per flowering stem.

*Tepals.*—About 2.5 cm in length and 4 mm in width, apex; acute, about 6 mm of distal region of tepals is unfused when flower is fully open, imbricate, base fused, margins entire on un-fused region, surface waxy, color on upper and lower surfaces 155C and 138C at apex.

*Flower buds.*—Oblong in shape, color 155C and 138A towards apex, an average of 2.1 cm in length and up to 5 mm in width.

*Peduncle.*—Arises from leaf node at center of leaf, about 8 mm in length and 1 mm in width, 138A in color, waxy surface, 1 per leaf node.

*Pedicels.*—2 to 3 per peduncle, about 5 to 7 mm in length, about 1 mm in width, 138A in color, waxy surface.

Reproductive organs:

*Gynoecium.*—1 pistil, style; 2.1 cm in length, <1 mm in width, 155C in color, stigma; papillose, 155C in color, ovary; superior, 1-locular, 3 mm in length and 2 mm in width, 138D in color.

*Androcoecium.*—6 stamens, filaments; adnate to tepals, 1.3 cm in length, <1 mm in width and 155C in color, anthers; dorsifixed, longitudinal dehiscence, 155A in color, pollen; sparse in quantity, very fine and 3D in color.

*Fruit.*—Globose berry, present in mid summer, about 1 cm in diameter, color; emerging 136A with shades of 136B, maturing to 103A, glaucous surface, flesh 146C.

*Seeds.*—18B in color, 8 to 12 per fruit, about 4 to 5 mm in diameter, basically round in shape with one side flattened.

It is claimed:

1. A new and distinct cultivar of *Polygonatum* plant named 'Prince Charming' substantially as herein illustrated and described.

* * * * *